United States Patent
Hudson, Jr. et al.

(10) Patent No.: US 11,337,918 B2
(45) Date of Patent: May 24, 2022

(54) METHOD AND SYSTEM FOR MAKING PERSONALIZED NUTRITIONAL AND PHARMACEUTICAL FORMULATIONS USING ADDITIVE MANUFACTURING

(71) Applicant: OneFul Health, Inc., Research Triangle Park, NC (US)

(72) Inventors: Edison Thurman Hudson, Jr., Researh Triangle Park, NC (US); Lloyd Staton Noel, III, Research Triangle Park, NC (US); Robert Eugene Hughes, Research Triangle Park, NC (US)

(73) Assignee: ONEFUL HEALTH, INC., Research Triangle Park, NC (US)

( * ) Notice: Subject to any disclaimer, the term of this patent is extended or adjusted under 35 U.S.C. 154(b) by 0 days.

(21) Appl. No.: 17/038,296

(22) Filed: Sep. 30, 2020

(65) Prior Publication Data
US 2021/0007981 A1      Jan. 14, 2021

Related U.S. Application Data

(63) Continuation of application No. PCT/US2019/025098, filed on Apr. 1, 2019.
(Continued)

(51) Int. Cl.
*A61K 9/00* (2006.01)
*B33Y 10/00* (2015.01)
(Continued)

(52) U.S. Cl.
CPC .......... *A61K 9/0056* (2013.01); *A23G 3/0072* (2013.01); *A23G 3/203* (2013.01);
(Continued)

(58) Field of Classification Search
CPC ...... A61K 9/00; A61K 31/525; A61K 31/455; A61K 31/197; A61K 31/44;
(Continued)

(56) References Cited

U.S. PATENT DOCUMENTS

| 6,013,282 A | 1/2000 | Mehra et al. |
| 2003/0203027 A1 | 10/2003 | Verreck et al. |

(Continued)

FOREIGN PATENT DOCUMENTS

| AU | 2014248516 | * 10/2015 | |
| AU | 2014248516 A1 | * 10/2015 | .............. A61J 1/062 |

(Continued)

OTHER PUBLICATIONS

Kathpalia et al "Development and Evalutation of a Ready to Use Paediatric Antibiotic Suspension", IJAPN / Apr.-Jun. 2011/vol. 1 / Issue. 2 / 71-77. (Year: 2011).*

(Continued)

*Primary Examiner* — Melissa S Mercier
(74) *Attorney, Agent, or Firm* — NK Patent Law

(57) ABSTRACT

The presently disclosed subject matter is directed to a system and method of preparing personalized nutritional and/or pharmaceutical formulations using additive manufacturing technology. Active pharmaceutical or dietary supplement ingredients are suspended in thixotropic stable carrier medias. The thixotropic suspensions are deposited onto a surface of a solid substrate, which can be a snack bar or small wafer used as a mechanical carrier. The disclosed system enables each additive active ingredient to be variably dosed based on a formula that is determined for each specific individual and manufactured on demand. Once the active ingredients are deposited on substrate, the entire assembly (Continued)

can be enrobed with one or more edible solid coatings to seal the active ingredients and provide taste-masking agent characteristics to the assembly.

22 Claims, 6 Drawing Sheets

Related U.S. Application Data

(60) Provisional application No. 62/655,280, filed on Apr. 10, 2018.

(51) Int. Cl.
| | |
|---|---|
| *B33Y 80/00* | (2015.01) |
| *A23P 20/15* | (2016.01) |
| *A23G 3/34* | (2006.01) |
| *A23G 3/20* | (2006.01) |
| *A61K 31/07* | (2006.01) |
| *A61K 31/197* | (2006.01) |
| *A61K 31/375* | (2006.01) |
| *A61K 31/4188* | (2006.01) |
| *A61K 31/44* | (2006.01) |
| *A61K 31/4415* | (2006.01) |
| *A61K 31/455* | (2006.01) |
| *A61K 31/519* | (2006.01) |
| *A61K 31/525* | (2006.01) |
| *A61K 31/714* | (2006.01) |

(52) U.S. Cl.
CPC ............ *A23G 3/2007* (2013.01); *A23P 20/15* (2016.08); *A61K 31/07* (2013.01); *A61K 31/197* (2013.01); *A61K 31/375* (2013.01); *A61K 31/4188* (2013.01); *A61K 31/44* (2013.01); *A61K 31/4415* (2013.01); *A61K 31/455* (2013.01); *A61K 31/519* (2013.01); *A61K 31/525* (2013.01); *A61K 31/714* (2013.01); *B33Y 10/00* (2014.12); *B33Y 80/00* (2014.12)

(58) Field of Classification Search
CPC .............. A61K 31/4188; A61K 31/519; A61K 31/714; A61K 31/07; A61K 31/375; A23P 20/15; B33Y 10/00; B33Y 80/00; A23G 3/34; A23G 3/20

See application file for complete search history.

(56) References Cited

U.S. PATENT DOCUMENTS

| | | | |
|---|---|---|---|
| 2008/0014302 A1 | 1/2008 | Elejalde et al. | |
| 2011/0293795 A1* | 12/2011 | Vaman | A23G 4/205 426/103 |
| 2016/0361335 A1 | 12/2016 | Jacob et al. | |

FOREIGN PATENT DOCUMENTS

| | | |
|---|---|---|
| CN | 205459955 U | 8/2016 |
| WO | 2010089767 A1 | 10/2003 |
| WO | 2008100032 A1 | 8/2008 |
| WO | 2011079302 A2 | 6/2011 |
| WO | 2011079302 A3 | 6/2011 |

OTHER PUBLICATIONS

Rossini et al. "Changes in the color of white chocolate during storage: potential roles of lipid oxidation and non-enzymatic browning reactions"; J Food Sci Technol (May-Jun. 2011) 48(3):305-311). (Year: 2011).*

WIPO; International Preliminary Report on Patentability for International Patent Application No. PCT/US2019/025098 dated Oct. 13, 2020, 9 pages.

ISA/KR; International Search Report and Written Opinion for International Patent Application No. PCT/US2019/025098 dated Jul. 16, 2019, 13 pages.

EPO; Extended European Search Report for European Patent Application No. 19784750.2 dated Nov. 24, 2021, 9 pages.

Chen, Lingyun and Muriel Subirade. Elaboration and Characterization of Soy/Zein Protein Microspheres for Controlled Nutraceutical Delivery. Biomacromolecules, vol. 10, 2009, 3327-3334. American Chemical Society. DOI: 10.1021/brn900989y.

* cited by examiner

METHOD AND SYSTEM FOR MAKING PERSONALIZED NUTRITIONAL AND PHARMACEUTICAL FORMULATIONS USING ADDITIVE MANUFACTURING

CROSS-REFERENCE TO RELATED APPLICATIONS

This application is a continuation application of International Patent Application No. PCT/US19/25098, filed on Apr. 1, 2019, which claims the benefit of U.S. Provisional Patent Application No. 62/655,280, filed on Apr. 10, 2018, the entire contents of which are all hereby incorporated herein by reference.

TECHNICAL FIELD

The presently disclosed subject matter relates to a method and system for making personalized nutritional and pharmaceutical formulations using additive manufacturing.

BACKGROUND

Two of the biggest problems facing the health care system are prescription non-adherence and "one size fits all" pharmaceutical formulations. The prevailing system for pharmaceutical treatment is to prescribe numerous pills and/or liquids of fixed doses to patients, oftentimes without feedforward information about the patient's medical history and personal biology. The patient is then relied upon to follow confusing daily and weekly medical regimens. This problem is known as "the pill burden," and is attributed to one of every twenty deaths in the United States. Problematically, the pill burden problem is exacerbated in populations that struggle with pill consumption (e.g., pediatrics and geriatrics), which are often the populations that need treatment the most. Thus, it would be beneficial to provide improved pharmaceutical consumption systems to overcome the cited challenges.

SUMMARY

In some embodiments, the presently disclosed subject matter is directed to a thixotropic suspension comprising one or more active ingredients, including drugs or nutritional ingredients, to be used to deliver an oral dose of known concentration as a dispensed line applied to an edible solid substrate, such as a bar. In some embodiments, the thixotropic suspension comprises active drug and/or nutrient ingredients homogenously dispersed within an edible carrier medium that flows under pressure applied by a controlled dispenser. The active drug and/or nutrient ingredients can be contained in microspheres uniformly dispersed throughout the volume of the suspension.

In some embodiments, the thixotropic suspension can be formulated from ingredients generally recognized as safe, made from a variety of digestible proteins, fats, plant fibers, polysaccharides, starches, hydrocolloid, edible waxes, or any of these materials that form a gel or SOL matrix, such that it returns to a semi-solid state at rest, and liquifies under pressure.

In some embodiments, the disclosed thixotropic suspension has low water activity ($A_w$) and/or has been prepared aseptically to have low microbial load and/or so that the thixotropic suspension has stability for greater than 14 days under ambient room conditions.

In some embodiments, the presently disclosed subject matter is directed to an edible bar shaped solid constructed from a variety of digestible proteins, fats, plant fibers, phytonutrients, starches, polysaccharides, edible waxes, or combinations thereof bound together to form a substrate in a forming, extrusion, pressing, or molding process. The bar can include digestible ingredients and binders that exhibit low water activity to reduce microbial activity and promote shelf stability of the finished delivery form. In some embodiments, the bar can include pre-formed channels preformed to act as containment dams for thixotropic suspensions such that the interaction of the APIs active ingredients is eliminated. The bar can include a thin overcoating of edible material to minimize the seeping of active ingredients into the substrate over the course of time, thereby eliminating interactions between the APIs and the substrate.

In some embodiments, the presently disclosed subject matter includes one or more computer-controlled systems comprising sensors and actuators to accurately control a volume of a dispensed thixotropic composition onto the solid substrate controlling dispense pressure, volume, temperature of application, and synchronizing the relative motion of the dispenser system to the solid substrate so that the rate of flow supports the creation of a continuous bead of dispensing of the API composition.

In some embodiments, the presently disclosed subject matter can include an apparatus to uniformly coat the bar with edible material, (such as chocolate, honey, icing, gels), that has low $A_w$, resulting in microbial activity in ambient environments.

In some embodiments, the presently disclosed subject matter is directed to a computer-controlled dispenser that can be commanded to pressurize and cause flow of the thixotropic suspension of APIs to achieve a specific flow rate from a bulk storage container. The dispenser can have a deformable nozzle that acts as a check valve, allowing flow in a forward direction co-axial to the same direction of the pressure of the dispenser, and closing as a pinch valve stopping flow of the thixotropic suspension when the dispenser is controlled to reverse direction of flow. The nozzle can be removable as a module to be disposed or to be cleaned and sterilized for reuse.

The disclosed computer-controlled dispenser can include a computer-controlled temperature controller with a heater and/or cooler combination in proximal location near the dispenser check valve. The heater/cooler can be selected from a rapid response thermoelectric or Peltier device, and a temperature sensor RTD, thermocouple, IR non-contact optical sensor. The heater/cooler can be configured to measure the temperature of the flowing suspension prior to passing through the deformable nozzle to control optimal viscosity and flow rheology of the thixotropic suspension.

In some embodiments, the dispenser can include a controlled motion platform, carrying the substrate, aligned with the direction of flow from the controlled dispenser. In some embodiments, the platform can carry the dispenser above a stationary substrate, moving at a rate that coordinates the flow rate of thixotropic suspension with motion velocity and acceleration.

In some embodiments, the presently disclosed subject matter is directed to a computer control algorithm relating the velocity of motion and acceleration of the motion platform to the rate of rate of flow of the dispenser, such that the linear velocity of flow of thixotropic suspension equals or closely approximates that of the motion platform in the direction of travel.

In some embodiments, the presently disclosed subject matter is directed to an algorithm that translates a dosage formula for one or more APIs to a volume of thixotropic suspension compound based on concentration of the thixotropic suspension (e.g., mg/ml of dispersed API) as parameters to drive the dispensed volume and flow rate during the motion path of the motion platform to dispense the command dose of the active ingredient onto the substrate.

In some embodiments, the presently disclosed subject matter is directed to an algorithm for selecting the optimal concentration of the active ingredients (mg/ml), the exit diameter of the dispenser check valve in the motion platform to ensure that the dispensed line is constrained to the boundaries of the substrate plane and constraining preform features.

In some embodiments, the presently disclosed subject matter includes multiple platforms coordinated with dispensers, each dispensing a separate ingredient or ingredient combination to form a bead of thixotropic suspension on the corresponding solid substrate of controlled volume, such that multiple suspensions with different, unique active ingredients can be dispensed in parallel to create a combination therapy of multiple active ingredients.

In some embodiments, the disclosed system includes a computer-controlled actuated pump and valve sequencing mechanism to source the commanded volume of thixotropic suspension from a flexible walled bulk container (e.g., a sterile bag) to supply the commanded volume of suspension to the dispensers.

In some embodiments, the disclosed system includes a gravimetric weighing system to measure the change in mass of the bulk container of thixotropic suspension after each dispense is commanded, which signals the computer-controlled system to verify that the expected volume was dispensed by the dispenser. The weighing system can measure the change in mass of the substrate to verify that the commanded amount of thixotropic suspension was dispensed.

In some embodiments, the presently disclosed subject matter includes an actuated pump that can be commanded to withdraw the seals of the pump into an integrated cleaning chamber, where the seals and the body of the pumping actuator can be flooded with water or other cleaning fluids to ensure that the pump is cleaned in place without disassembly.

In some embodiments, the presently disclosed subject matter include a printable data symbol (e.g., QR code) attached to the container of the thixotropic suspension to identify the APIs embedded in the suspension. The symbol can point to a hyperlink location of data showing manufacturing parameter about the batch of the suspension including nominal concentration and density from formulation recipe, lab tested concentration and density, beyond use date, location of manufacture, certificate of analysis of the API, total mass, remaining mass, and any other data relevant to quality control of the API in the container.

In some embodiments, the presently disclosed subject matter is directed to a computer-based method of allowing the selection of a type of solid substrate based on responses or data about an individual to fulfill a need for the ingredients captured in the substrate preform, such as protein, fiber, fats, phytonutrients, etc. that have nutritive value, or that may be selected based on absence of allergens that would affect the individual.

In some embodiments, the presently disclosed system includes a computer-controlled actuator for each API commanded to a specified displacements, velocities, and accelerations as may be needed to provide the pressure that that is required for the suspension's viscosity, and to match the rheology, to obtain a controlled flow rate needed to form a continuous bead altered for the thixotropic suspension being dispensed. In some embodiments, the system can include multiple actuators that coordinate the displacement, velocities, and accelerations of each independent actuator such that the flow rate of all thixotropic suspension ingredients form beads at rate needed to match the relative motion to the substrate.

In some embodiments, the disclosed system includes a computer readable coding device or symbol attached to identify the thixotropic suspension in each container (e.g., bag) that can be read by the computer controller of multiple actuators to identify the suspension and a communications method to look up the suspension's rheological characteristics and parameters previously determined to command the actuator to which the suspension is assigned to move at the appropriate velocity, displacement rate, and acceleration to generate a pressure at a level to obtain the desired flow rate for dispensing.

In some embodiments, a machine vision or 3D volume scanner or structured light plane can be used on each bar to ensure that complete lines of correct volume are dispensed on the substrate, especially if without the containment channels on a planar substrate.

In some embodiments, the presently disclosed subject matter is directed to a solid assembly for oral consumption, the assembly comprising a solid substrate comprising a surface with one or more depressions. The assembly further comprises one or more thixotropic suspensions deposited within the depressions of the solid substrate, wherein each thixotropic suspension comprises a homogenous dispersion of one or more active pharmaceutical ingredients (APIs) and a carrier, and one or more coatings applied over one or more surfaces of the solid substrate. Each API is variably dosed based on a formula that is determined for each specific subject.

In some embodiments, the substrate is a solid at room temperature and atmospheric pressure. The substrate can be selected from a food product (e.g., chocolate, carob, peanut butter, butterscotch, fruit pomace, granola, whole or rolled oats, or combinations thereof), an excipient (one or more fillers, pH adjusting agents, preservatives, anti-adhesives, plasticizers, opacifiers, coloring agents, pigments, surfactants, diluents, anti-foaming agents, lubricants, binders, granulating aids, taste modifying agents, and glidants), or combinations thereof. The substrate can be configured as a bar, coupon, or wafer. In some embodiments, the substrate comprises a top surface that is planar. In some embodiments, the depressions are configured in the top surface of the substrate. In some embodiments, the depressions are configured as a plurality of longitudinal channels.

In some embodiments, the APIs are selected from one or more pharmaceuticals, vitamins, food supplements, or combinations thereof. The one or more pharmaceuticals can be selected from compounds used for prevention, diagnosis, treatment, or cure of a chronic condition (cardiovascular disease, type 2 diabetes, rheumatoid arthritis, or cancer). The vitamins can be selected from thiamine, riboflavin, niacin, nicotinic acid, pantothenic acid, pyridoxine, biotin, folic acid, vitamin $B_6$, vitamin $B_{12}$, lipoic acid, vitamin C, vitamin A, vitamin D, vitamin E, vitamin K, and derivatives thereof. The food supplements can be selected from iron, calcium, selenium, iodine, magnesium, BHT, BHA, flavonoids, beta carotene, polyphenol, glutathione, *echinacea*, flaxseed, gingko, turmeric, L-arginine, L-glutathione, L-lysine, and combinations thereof.

In some embodiments, the APIs can be encapsulated into microspheres. The microspheres can be selected from reservoir-type microspheres, matrix-type microspheres, or combinations of reservoir-type and matrix-type microspheres. The microspheres can have a size of about 1200 μm or less.

In some embodiments, the carrier is selected from gelatin, polymeric glycosaminoglycan, agar, carrageenan, alginate, natural gum, carboxymethyl cellulose, xylitol, sorbitol, mannitol, glycerin, pectin, dextran, dextran derivative, pullulan, xanthan, xyloglucan, starch, hyaluronic acid, guar gum, locust bean gum, gellan, carboxy-methyl-cellulose, acacia gum, propylene glycol, polyethylene glycol, polypropylene glycol, poly(tetramethylene ether) glycol, or combinations thereof. The carrier can be liquid or semi-solid. The carrier can have a water activity ($A_w$) of about 0.95 or less. The carrier can be aseptic.

In some embodiments, the one or more thixotropic suspensions have a shelf life of at least 14 days under refrigerated conditions of about 40° F. and/or of at least 300 days under refrigerated conditions of about 40° F.

In some embodiments, the one or more APIs are uniformly dispersed but undissolved within the carrier.

In some embodiments, the one or more coatings are solid or semi-solid. The coatings can be selected from chocolate, caramel, honey, nougat, syrup, nut butter, agave, syrup, yogurt, pudding, butterscotch, fruit purees, molasses, frosting, flavored polysaccharide films, marshmallow cream, and combinations thereof.

In some embodiments, the subject is an animal (e.g., a human).

In some embodiments, the presently disclosed subject matter is directed to a method of treating a medical condition, the method comprising administering a therapeutically effective amount of an active pharmaceutical ingredient (API) to a subject in need thereof, whereby the medical condition is treated. The API is configured in a solid assembly for oral consumption as disclosed herein. In some embodiments, the administering comprises eating the solid assembly.

In some embodiments, the presently disclosed subject matter is directed to a method of preparing a solid assembly for oral consumption, the method comprising depositing one or more thixotropic suspensions onto one or more depressions positioned on a surface of a solid substrate, wherein each thixotropic suspension comprises a homogenous dispersion of one or more active pharmaceutical ingredients (APIs) and a carrier; and applying one or more coatings to one or more surfaces of the solid substrate; wherein each API is variably dosed based on a formula that is determined for a specific subject. In some embodiments, the thixotropic suspensions are deposited using a computer-controlled dispenser (e.g., a servo actuator).

In some embodiments, the dispenser enables continuous beads of thixotropic compositions at known densities and concentrations of API ingredients to be dispensed. In some embodiments, the dispenser is configured to allow more than one thixotropic suspension to be dispensed in parallel. In some embodiments, the dispenser is configured to dispense a volume of thixotropic suspension that is proportional to the dose of API formulated for the subject. In some embodiments, the computer controls one or more of the thixotropic suspension's pressure, volume, or temperature. In some embodiments, the dispenser comprises a computer-controlled actuated pump configured to dispense a controlled volume of thixotropic suspension.

In some embodiments, the dispenser comprises an output from which the thixotropic suspension is dispensed, wherein the output comprises a deformable nozzle (e.g., a check valve).

In some embodiments, the dispenser comprises a gravimetric weighing device to measure the change in mass of a bulk container of thixotropic suspension after each dispense is commanded.

In some embodiments, the dispenser comprises a controlled motion platform that carries the substrate and moves at a rate that coordinates a flow rate of the thixotropic suspension during dispensing.

In some embodiments, the dispenser comprises one or more temperature sensors and a heater, cooler, or both to monitor the temperature of the thixotropic suspension during dispensing, and to heat or cool the suspension to a desired temperature. In some embodiments, the sensor is positioned next to an exit nozzle of the dispenser.

In some embodiments, the computer employs an algorithm relating the velocity of motion and acceleration of the computer-controlled motion platform to the rate of flow of the dispenser.

In some embodiments, the computer employs an algorithm that translates a dosage formula for one or more APIs to a volume of thixotropic suspension based on the concentration of the suspension.

In some embodiments, the presently disclosed subject matter is directed to a system for producing a solid assembly for oral consumption, the solid assembly comprising a solid substrate comprising a surface with one or more depressions; one or more thixotropic suspensions deposited within the depressions of the solid substrate, wherein each thixotropic suspension comprises a homogenous dispersion of one or more active pharmaceutical ingredients (APIs) and a carrier; one or more coatings applied over one or more surfaces of the solid substrate; wherein each API is variably dosed based on a formula that is determined for each specific subject; wherein the system comprises a computer-controlled dispenser.

BRIEF DESCRIPTION OF THE DRAWINGS

The previous summary and the following detailed descriptions are to be read in view of the drawings, which illustrate some (but not all) embodiments of the presently disclosed subject matter.

FIG. 1b is a cross-sectional view of the assembly of FIG. 1a.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a carrier" can include a plurality of such carriers, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1A:
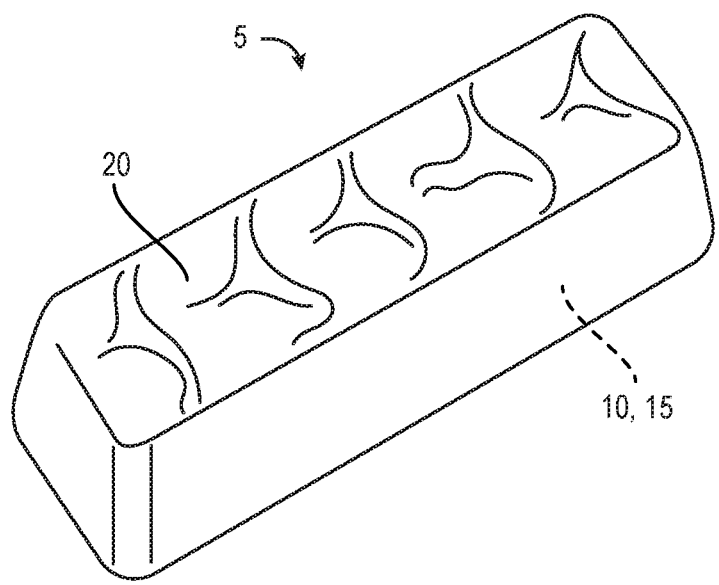
FIG. 1a is a perspective view of an edible assembly in accordance with some embodiments of the presently disclosed subject matter.
Figure 1B:
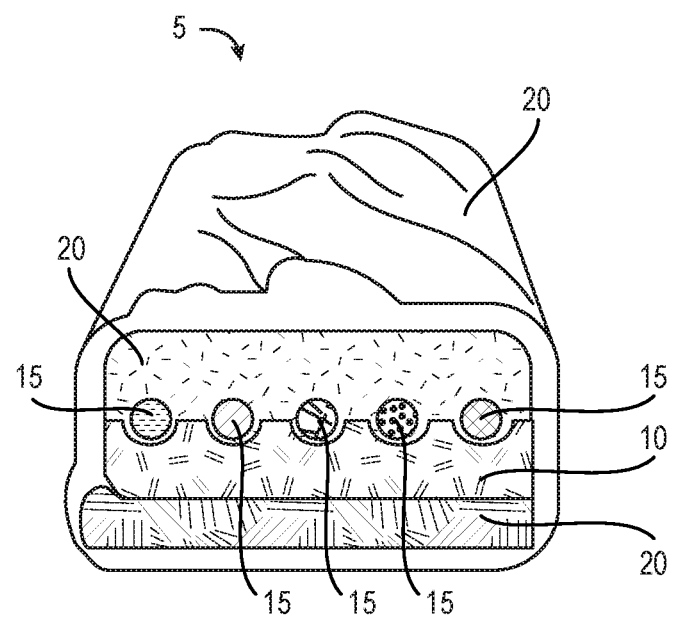

The presently disclosed subject matter is directed to a system and method of preparing solid personalized nutritional and/or pharmaceutical formulations using additive manufacturing technology. Active pharmaceutical and/or dietary supplement ingredients (referred to as "APIs") are suspended in thixotropic stable carrier medias. As shown in FIGS. 1a and 1b, one or more nutritional and/or pharmaceutical formulations are provided as solid assembly 5, which in some embodiments can be a snack bar or small wafer. The term "solid" as used herein refers to a material that will not flow or is not fluid. The disclosed solid assembly includes substrate 10 constructed from a food product or other edible excipient used as a mechanical carrier. One or more additive-comprising thixotropic suspensions 15 are additively deposited onto a surface of substrate 10. The disclosed system enables each API to be variably dosed based on a formula that is determined for each specific individual and manufactured on demand. Once one or more thixotropic suspensions 15 are deposited onto substrate 10, it can be enrobed with one or more edible solid coatings 20 to seal the APIs from air, moisture exposure, and/or contamination. Advantageously, coating 20 has a pleasing flavor and acts as a taste-masking agent and inducement for daily adherence of the APIs.

Figure 2A:
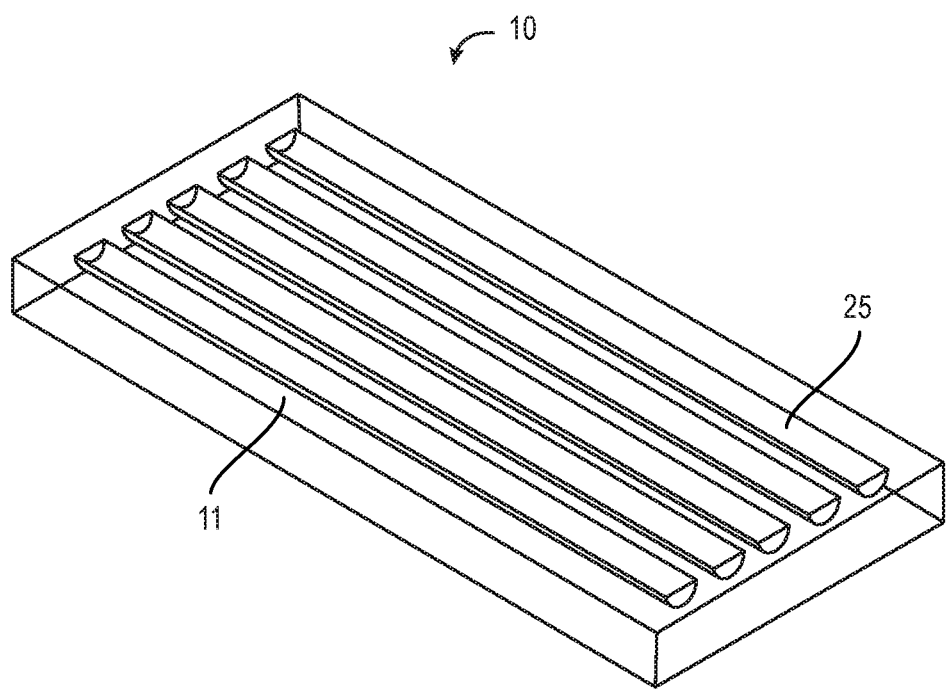
FIGS. 2a and 2b are perspective views of substrates in accordance with some embodiments of the presently disclosed subject matter.
Figure 2B:
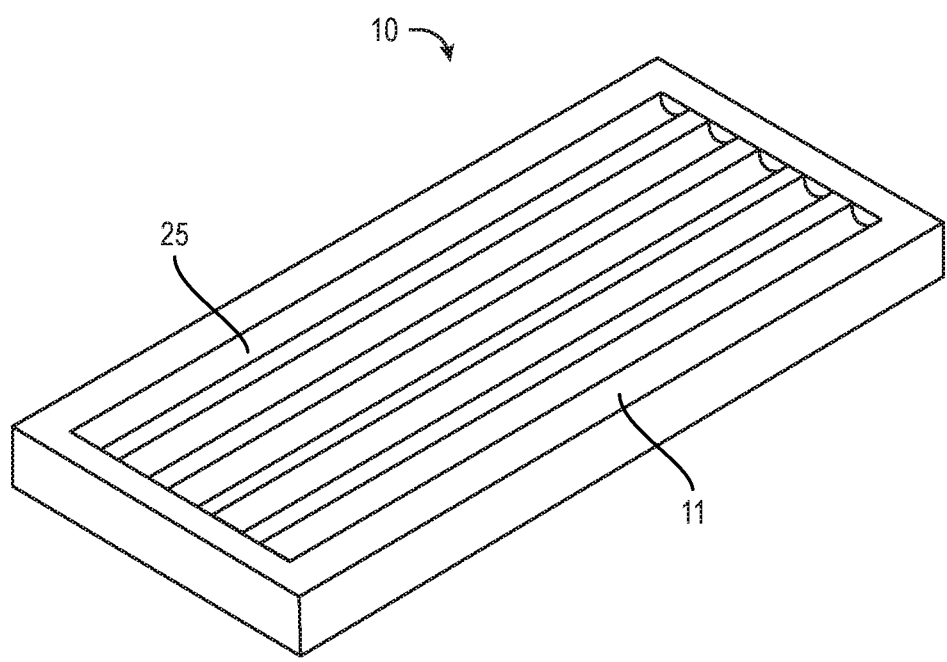

FIGS. 2a and 2b illustrate one embodiment of substrate 10. As disclosed above, the substrate is provided as a solid at room temperature and atmospheric pressure. Substrate 10 is constructed from an edible material with sufficient rigidity to maintain its form. Suitable edible substrates can be selected from food products and/or excipients. The term "food product" refers to any consumable solid matter. Food products suitable for use as substrate 10 can include (but are not limited to) solid forms of chocolate, carob, peanut butter, butterscotch, fruit pomace, granola, rolled and whole grain oats, chicory root extract, fiber-containing wafers, and the like.

The term "excipient" as used herein refers to a compound or composition that is not intended to have medicinal activity. Examples of suitable excipients include (but are not limited to) fillers, pH adjusting agents, preservatives, anti-adhesives (such as talc), plasticizers (such as polyethylene glycol, castor oil, diacetylated monoglycerides, dibutyl sebacate, diethyl phthalate, glycerin, propylene glycol, triacetin, polysorbates, sorbitan esters, and/or triethyl citrate), opacifiers (such as titanium dioxide, talc, aluminium silicate, magnesium carbonate, calcium sulfate, and/or aluminium hydroxide), coloring agents, pigments, surfactants (such as alkali metal or alkaline earth metal salts of fatty acids, polyoxyethylenated oils, polyoxyethylenelpolyoxypropylene copolymers, polyoxyethylenated sorbitan esters, polyoxyethylenated castor oil derivatives, stearates, polysorbates, stearylfumarates, glycerol behenate, benzalkonium chloride, and/or acetyltrimethylammonium bromide) diluents, anti-foaming agents, lubricants, binders, granulating aids, taste modifying agents, and/or glidants that are conventional in the pharmaceutical art. In some embodiments, the excipients are hydrophobic (e.g., waxes or lipids), hydrophilic, enteric-release, and/or naturally derived.

The substrate can be formed in any desired shape, such as (but not limited to) square, rectangular, oval, round, abstract, and the like. For example, the substrate can be configured as a bar, coupon, or wafer. In some embodiments, top surface 11 of substrate 10 can be substantially planar (e.g., flat and two-dimensional). However, the shape of the top surface is not limited and can be configured as substantially non-planar in some embodiments. The "top surface" of the substrate refers to the surface facing upwards when the substrate is placed on a support, such as a table.

As described above, one or more viscous or thixotropic API-comprising suspensions are deposited onto a surface of substrate 5. As illustrated in FIGS. 2a and 2b, in some embodiments, at least one surface of the substrate (e.g., top surface 11) can include one or more depressions 25 onto which the viscous or thixotropic suspensions are deposited. The depressions can be configured in any desired shape, including (but not limited to) channels, pockets, grooves, apertures, or combinations thereof. For example, in some embodiments, the depressions can be configured as one or more longitudinal channels that act as containment dams to eliminate interaction of the APIs within the viscous or thixotropic suspensions. Further, when the APIs are configured as low viscosity materials that tend to flow, the depressions maintain the API within a desired area.

Edible substrate 10 can be constructed using any method known or used in the art. For example, the substrate can be formed using injection molding technology. Particularly, a predetermined amount of substrate in a flowable state (e.g., melted or partially melted) can be deposited into a mold. The substrate is then cooled to room temperature and solidified within the mold, taking the shape of the mold interior once removed. However, it should be appreciated any known method can be used to form substrate 10, such as forming, extrusion, pressing, and the like.

One or more active pharmaceutical or nutritional ingredients ("APIs") are suspended in edible carriers that are deposited onto a surface of substrate 10 (e.g., into depressions 25). Suitable APIs can include orally administered pharmaceuticals, vitamins, food supplements, and combinations thereof. For example, suitable pharmaceuticals can include any of the wide variety of chemical compounds that can be used for prevention, diagnosis, treatment, and/or cure of a medical condition. In some embodiments, the pharmaceutical can be used to treat a chronic condition, such as (but not limited to) cardiovascular disease, type 2 diabetes, rheumatoid arthritis, and/or some forms of cancer.

Suitable APIs can also include one or more vitamins, such as thiamine, riboflavin, niacin, nicotinic acid, pantothenic acid, pyridoxine, biotin, folic acid, vitamin $B_6$, vitamin $B_{12}$, lipoic acid, vitamin C, vitamin A, vitamin D, vitamin E, vitamin K, and derivatives thereof.

Suitable APIs can also include food supplements, including any of the wide variety of ingestible compositions that affect the response of the body to a food and/or enhance the quality of a food, such as (but not limited to) minerals, antioxidants, botanicals, amino acids, and combinations thereof. For example, in some embodiments the food supplement can be selected from the group comprising iron, calcium, selenium, iodine, magnesium, BHT, BHA, flavonoids, beta carotene, polyphenol, glutathione, *echinacea*, flaxseed, gingko, turmeric, L-arginine, L-glutathione, L-lysine, and combinations thereof.

In some embodiments, the APIs can be encapsulated into microspheres that are dispersed within the thixotropic carrier. In some embodiments, the microspheres can be of the reservoir type (e.g., marked by one or more film coatings surrounding an inner core of active material, also called a "core shell microparticle"). Alternatively, the microspheres can be of the matrix type, marked by an inhomogeneous single layer wherein the API is dispersed throughout an excipient and there is no film coating. In some embodiments, the microspheres can be a combination of a matrix particle and a reservoir particle, such as a matrix core with one or more film coatings. The microspheres can release therapeutically effective doses of immediate release, extended release, modified release, and/or delayed release API profiles in vitro and in vivo. Advantageously, microspheres modify the diffusion and dissolution kinetics of the APIs, impart taste-masking properties, deliver therapeutically effective doses, and protect the APIs during processing and storage.

The API microspheres can be prepared using any method known or used in the art. For example, the microspheres can be prepared using centrifugal extrusion of waxes, lipids, or oils with dissolved or dispersed APIs that are optionally coated in a fluidized bed with a Wurster or powder-coating insert to apply a diffusion barrier and/or enteric coating. In some embodiments, the microspheres can be constructed using spheronization of the APIs by coating inert cores (such as sugar or microcrystalline cellulose spheres) with powder APIs granulated with binders and/or excipients in a high-shear powder-coating fluidized bed and/or Wurster fluidized bed to produce an API matrix particle. In some embodiments, the particles can be further coated in a fluidized bed with a Wurster or powder-coating insert to apply a diffusion barrier and/or enteric coating. The API microspheres can have a size of about 1200 µm or less, such as about 10-1000 µm, 25-800 µm, 50-600 µm, 75-500 µm, or 100-450 µm. However, the term "microsphere" is not limited to a particular size and the presently disclosed subject matter can include microspheres with sizes larger and smaller than the ranges recited herein.

The APIs are homogeneously distributed within a thixotropic carrier (e.g., as a bulk powder), creating suspension 15 at rest and at certain temperature ranges (e.g., greater than 50° C. and less than 125° C.). The term "thixotropic" as used herein refers to a shear-thinning property, where a gel or liquid becomes less viscous when shaken, agitated, or otherwise stressed. In some embodiments, the term "thixotropic" includes viscous materials. Thixotropic suspensions can be aqueous-based (e.g., hydrocolloids), lipid-based (e.g., oleogels), or emulsions. The term "oleogel" refers to structured networks of edible oils that exhibit solid-like properties. Although saturated fats and trans fats also display solid-like characteristics at room temperature, these fats are often associated with negative health effects. Oleogels allow for the use of liquid oils that comprise high amounts of healthier unsaturated fatty acids that display solid-like rheological properties when mixed with gelling agents, such as plant waxes (canuba wax, candelilla wax, sunflower wax, rice bran wax, etc.) or food-grade polymers (ethyl-cellulose, etc.). Thus, oleogels provide desirable characteristics, such as increased viscosity to prevent settling, as well as provide a stabilizing micro-environment for water-sensitive ingredients.

The carrier can include any of the wide variety of thixotropic materials known in the art. In some embodiments, suitable thixotropic carriers can comprise one or more polyols, lipids, and/or semi-solid media. The term "semi-solid" refers to a composition that is a mixture of liquid and solid phases, having a viscosity of about 40,000-800,000 centipose. In some embodiments, the carrier can comprise a hydrocolloid or other edible polymer matrix. The term "hydrocolloid" as used herein refers to molecules that are dispersible in water or an aqueous solution. Thus, the suspending media can comprise gelatin, polymeric glycosaminoglycans, agar, carrageenan, alginate, natural gums, carboxymethyl cellulose, xylitol, sorbitol, mannitol, glycerin, pectin, dextran, dextran derivatives, pullulan, xanthan, xyloglucan, starch, hyaluronic acid, guar gum, locust bean gum, gellan, carboxy-methyl-cellulose, acacia gum, propylene glycol, polyethylene glycol, polypropylene glycol, poly (tetramethylene ether) glycol, and/or combinations thereof. In some embodiments, the carrier can be liquid or semi-solid.

In some embodiments, the carrier mediums are formulated to have low water activity (low $A_w$) to achieve reduced microbial activity, suppressing the growth of bacteria, fungi, molds, and the like. For example, the water activity can be in the range of about 0.95 or less (e.g., 0.95, 0.9, 0.85, 0.8, 0.75, 0.7, 0.65, 0.6, 0.55, 0.5, 0.45, 0.4, 0.35, 0.3, 0.25, or less). Alternatively or in addition, the thixotropic carriers can be thermally treated to achieve an aseptic level of sterilization prior to the embedding and distribution of APIs. As a result, the API suspensions can be aseptic. The term "aseptic" as used herein refers to processing conditions that inhibit or prevent contamination by external pathogenic microorganisms and/or undesired exogenous materials. In some embodiments, the thixtropic carrier suspensions can have a shelf-life of at least about 14 days, such as at least about 14, 20, 30, 40, 50, 60, 70, 80, 90, 100, 110, 120, 130, 140, 150, 160, 170, 180, 190, 200, 210, 220, 230, 240, 250, 260, 270, 280, 290, or 300 days.

Optional ingredients can be included within the disclosed microspheres and/or carriers, such as (but not limited to) flavorings, colorings, preservatives, and the like. For example, the carrier can include one or more preservatives to reduce and/or prevent microbial growth. In addition, the carrier can optionally include one or more additional agents and/or polymer structures that mechanically or chemically preserve the integrity of the APIs or microspheres, thereby minimizing leaks of the APIs.

The homogeneous distribution of one or more APIs within the carrier creates thixotropic suspension 15. The suspension has a homogenous density, such that a known volume contains a tested mass of APIs per unit volume. Thixotropic suspension 15 can be in a semi-solid state at rest, and liquified under pressure. The disclosed suspensions can take a finite time to return to equilibrium viscosity after a steep change in shear rate typically induced by pressure that converts it to a fluid. The thixotropic compositions primarily used in disclosed system return to their semi-solid or gel state rapidly, as pseudo-plastic fluids.

Thus, thixotropic semi-solid or liquid suspension 15 has properties that enable the dissolution or suspension of the APIs in a form that is stable until agitated or extruded, at which point the suspension becomes fluid and can be dispensed. In some embodiments, the thixotropic suspensions are formed via molecular self-assembly of cross-linked polymers, causing the APIs that are agitated with the vehicle to be embedded with a verifiable solution strength and uniform volumetric concentration of ingredients to function as the components in the building of customized formulations. The suspending carrier media behaves as a semi-solid with nearly uniform dispersion of the APIs within the 3-D suspension network.

The disclosed viscous or thixotropic suspensions can be individually formulated for a particular subject, based on the subject's medical history. For example, a single dosage of a particular API can be suspended in the carrier. In some embodiments, more than one API can be dispersed in a single carrier (e.g., when the APIs do not interact). The disclosed suspensions have a homogeneity that enables the APIs to be uniformly dispersed but undissolved within the suspension media. For example, in embodiments wherein the APIs have been microencapsulated in microspheres, they are kinetically restrained from saturating the carrier. As a result, the APIs remain unmixed (or nearly unmixed), therapeutically effective, and do not agglomerate after processing (e.g., through shear thinning during dispensing) and/or prolonged storage.

The disclosed viscous or thixotropic suspension is pumpable and flowable. As a result, the precise and variable volumetric dispensing of small volumes of the suspension can be achieved. The suspension remains uniform or about uniform during volumetric dispensing of the APIs or microspheres.

Figure 3A:
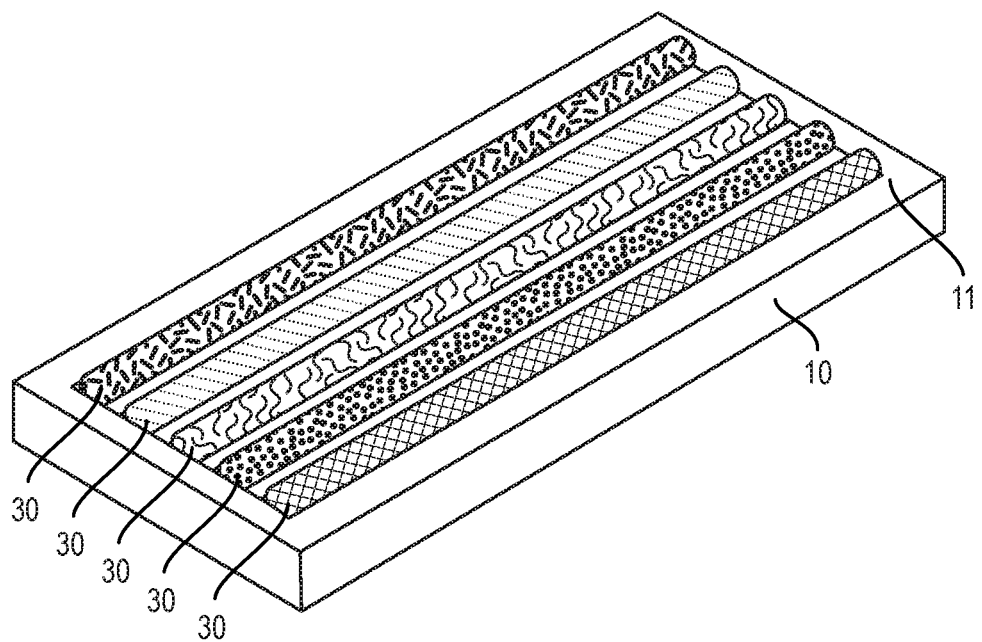
FIGS. 3a and 3b are perspective views of substrates comprising a plurality of thixotropic suspensions in accordance with some embodiments of the presently disclosed subject matter.
Figure 3B:
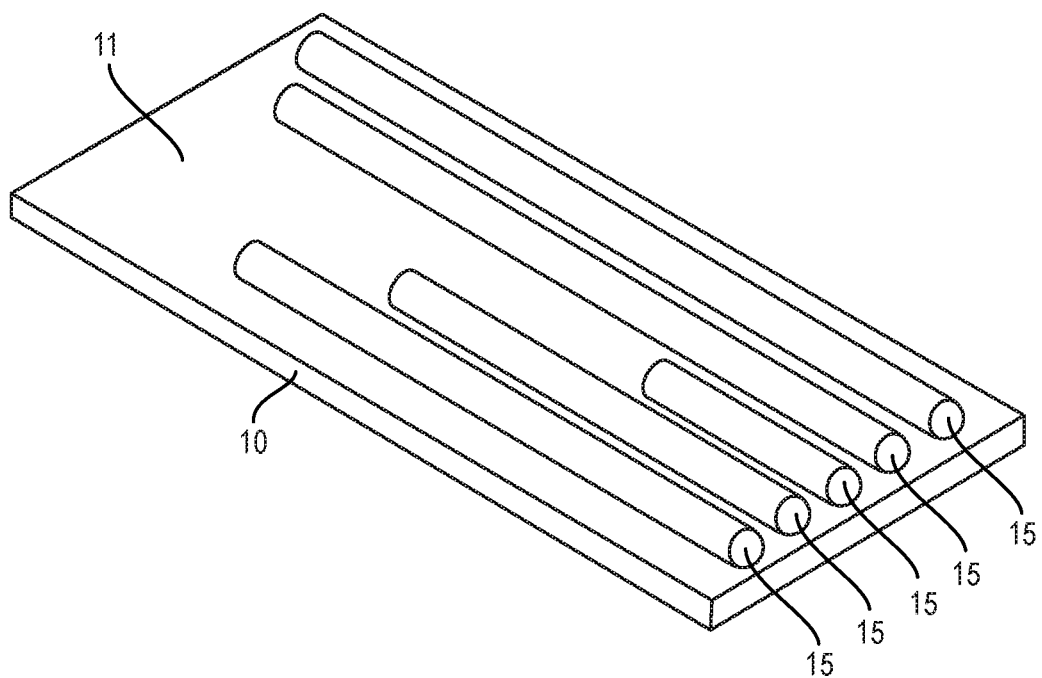

As set forth above, one or more viscous and/or thixotropic suspensions 15 are deposited onto a surface of substrate 10. In some embodiments, the suspension can be dispensed as a longitudinal bead. As shown in FIG. 3a, the suspensions can be deposited onto depressions 25 located on top surface 11 of the substrate. In some embodiments, each individual thixotropic suspension 15 differs from the remainder of the suspensions with regard to carrier used, API identification, and/or API concentration. Thus, a customized suspension of each API at known density and concentration can be deposited onto substrate 10. Depending on the concentration of each API, not every suspension 15 deposited onto the substrate will have the same volume. For example, as illustrated in FIG. 3b, the volumes of each suspension can vary.

Further, in some embodiments, the thixotropic suspensions can be stacked to achieve a higher total number of ingredients. For example, a 3-layer×5 line bar can have 15 ingredients, or a 6 line 2-layer bar can have 12 ingredients. It should be appreciated that there are many trade offs and optimizations that can be calculated to achieve a total desired dose and number of APIs in an assembly (e.g., bar).

Suspensions 15 can be deposited onto a surface of the substrate using any method known or used in the art. For example, as set forth in detail below, the APIs can be dosed in variable volumes using one or more embodiments of a computer-controlled dispenser. The viscous and/or thixotropic suspensions include known densities and concentrations of APIs and therefore can be controlled and dispensed at known concentrations. In this way, the total volume of the suspension dispensed (or the depressions filled) matches the volume of prescribed doses based on a known mass of the APIs per unit volume. The concentration of the APIs per unit volume can be determined by known formulations and quantified by lab assays of the produced batch (e.g., HPLC, mass spectrometry). The concentration can then be recorded to a data store that can be retrieved by the additive automation.

Further, the dispensed beads (lines) of API are consistent from multiple channels. Prior art methods employ 3D printing systems that cannot achieve consistent lines.

In some embodiments, a digitally controlled computer servo actuator can be used to dose thixotropic suspensions 15 onto a surface of the substrate (e.g., into depressions 25). Particularly, continuous beads of thixotropic compositions at known densities and concentrations of API ingredients can be controlled and dispensed. The system can therefore apply high accuracy, controlled extrusion methods for one or multiple ingredients in parallel onto substrate 10. The volume dispensed is proportional to the dose of API formulated for a specific individual. Furthermore, as a closed loop control of dispensing, gravimetric measurements of the added mass enable quality by design to confirm that the expected mass of carrier is dispensed to the substrate. Thus, the disclosed system enables individualized dosing of active ingredients using computer-served and controlled extrusion and dispensing.

In some embodiments, a computer-controlled actuator for each thixotropic suspension can be commanded to a specific displacement, velocity, and acceleration as may be needed to provide the pressure that is required for the particular velocity, and to match the rheology, to obtain a controlled flow rate needed to form a continuous bead altered of the API being dispensed by the dispenser. In some embodiment, the system can include multiple actuators that coordinate the displacement, velocity, and acceleration of each independent actuator such that the flow rate of all thixotropic suspensions form beads at the rate needed to match the relative motion to the substrate.

Figure 4A:
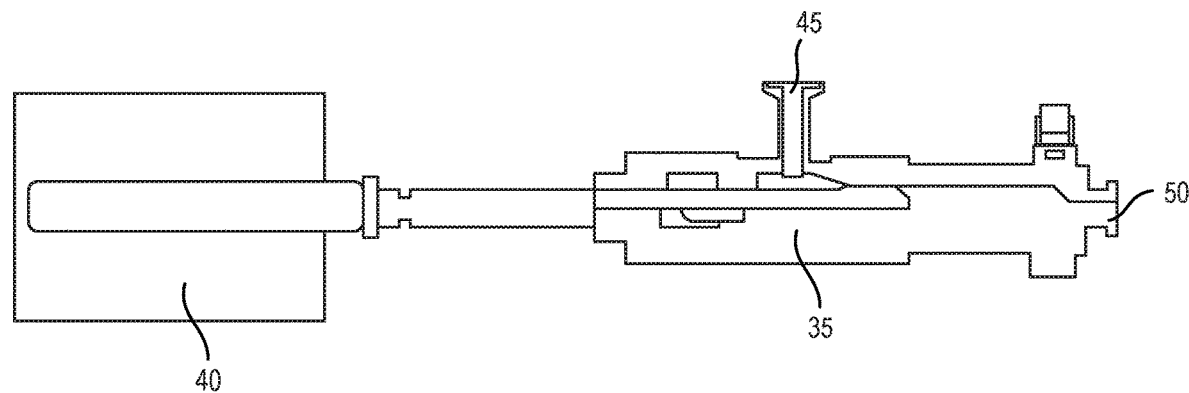
FIG. 4a is a side plan view of a dispenser and computer that can be used to dispense a thixotropic suspension in accordance with some embodiments of the presently disclosed subject matter.

FIG. 4a illustrates one embodiment of a dispenser that can be used to dispense the thixotropic suspensions onto substrate 10. Particularly, dispenser 35 can be regulated by computer 40 to control one or more dispensing parameters. For example, the computer can control the pressure, volume, and/or temperature of API application. In some embodiments, each thixotropic suspension enters the dispenser through one or more ports 45 for dispensing. Thus, the controlled dispenser can include computer controls that can be initiated to pressurize and begin flow of the thixotropic suspension to achieve a desired flow rate from a bulk storage container. In this way, a controlled volume of flow of the thixotropic suspension is dispensed. In some embodiments, the disclosed system can include a computer-controlled actuated pump and valve sequencing mechanism to source the commanded volume of thixotropic suspension from the bulk container to supply the commanded volume of suspension to the dispenser. In some embodiments, the bulk container can have one or more flexible walls, such as a sterile bag.

Figure 4B:
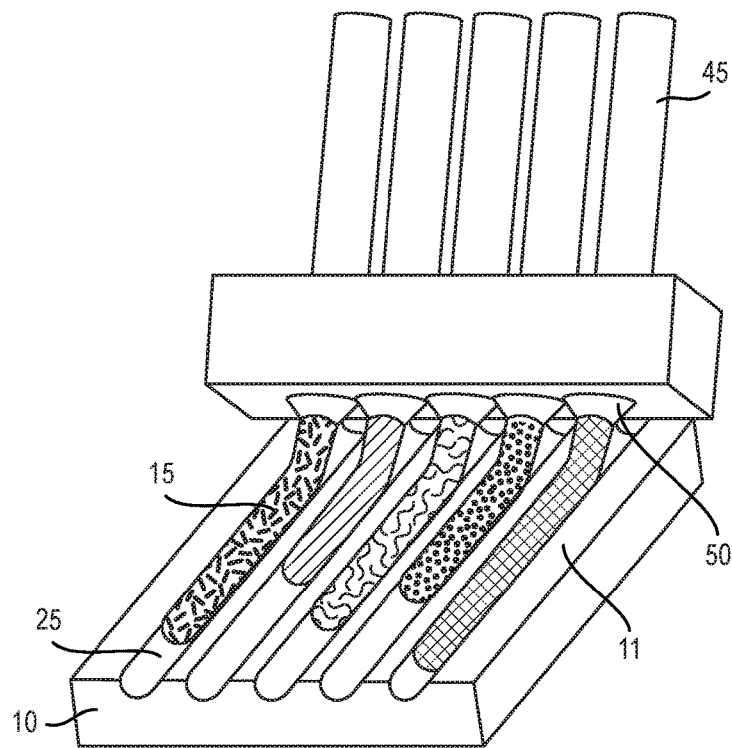
FIG. 4b is a perspective view illustrating one embodiment of a dispenser dispensing a thixotropic suspension onto a substrate.

The suspension is dispensed through output 50 onto the substrate, as illustrated in FIG. 4*b*. In some embodiments, the output can be a deformable nozzle that acts as a check valve, allowing flow in a forward direction co-axial to the direction of the pressure of the dispenser. In some embodiments, the output ceases as a result of a pinch valve stopping flow of the thixotropic suspension when the dispenser reverses the direction of flow. Advantageously, the deformable nozzle can be removed in some embodiments for disposal or to allow cleaning and/or sterilization. However, it should be appreciated that the disclosed system is not limited and any known method or apparatus can be used to dispense the suspensions onto substrate 10.

In some embodiments, the disclosed system can include a gravimetric weighing device to measure the change in mass of the bulk container of thixotropic suspension after each dispense is commanded. After each change in mass, the system is signalled to verify that the expected volume was dispensed by the dispenser. In some embodiments, the change in mass of the substrate can be measured to verify that the commanded amount of thixotropic suspension was dispensed to the substrate.

A printable data symbol (e.g., QR code) can be attached to the thixotropic suspension container to identify the particular API embedded in the suspension. In some embodiments, the symbol can include a hyperlink location of data showing manufacturing parameters associated with the batch of the suspension, including nominal concentration, density from formulation recipe, lab tested concentration and density, expiration date, location of manufacture, certificate of analysis of the API, total mass, remaining mass, and any other data relevant to quality control of the API.

Thus, in some embodiments, the system can include a computer readable coding device or symbol that can be used to identify the thixotropic suspension in each container (e.g., bag) that is read by the computer controller of multiple actuators. The system can include a communications method to look up the thixotropic suspension's rheological characteristics and parameters previously determined to command the actuator to which the thixotropic suspension is assigned to move at the appropriate velocity, displacement rate, and acceleration to generate a pressure on the thixotropic suspension at a level to obtain the desired flow rate for dispensing.

In some embodiments, computer 40 can synchronize the motion of the dispenser system relative to the substrate so that the rate of flow supports the creation of a continuous bead of API suspension. To this end, the dispenser can include a controlled motion platform that carries substrate 10. The platform can be aligned with the direction of flow from the controlled dispenser, or alternatively a controlled motion platform that carries the dispenser above a stationary substrate, moving at a rate that coordinates flow rate of the thixotropic suspension with motion velocity and acceleration.

It is important to assure quality of the assembly that the proper amount of API is dispensed. Further, the continuity of the bead must be maintained (e.g., no breaks and/or thin segments). The continuity of dispensing can be determined by machine vision inspection, either on the fly as dispensed or by an image taken after each bar is dispensed. For example, grayscale and color 2D processing can be used for many materials. Further, 3D inspection can be used in some embodiments to consistently measure volume. Thus, a simple 2.5 D method using a plane of light (laser or white) intersecting the bead as a cross-section that is imaged from above the bar as it moves past the intersection of the plane of light and the image. This method can be used to assure that each bead is fully dispensed and to ensure that the correct dose of each API is applied. Bars that have defective levels of API can then be easily rejected.

In some embodiments, the dispenser has computer-controlled temperature features, and comprises a heater and/or cooler positioned near the exit nozzle. In this way, optimal viscosity and flow rheology of the thixotropic suspension can be controlled. In some embodiments, the heater and/or cooler can be a rapid response thermoelectric or Peltier device. The dispenser can therefore include one or more sensors to measure and/or record the temperature of suspension 15. Any known sensor can be used, such as a temperature sensor RTD, thermocouple, and/or IR non-contact optical sensor.

The disclosed system can employ a computer control algorithm relating the velocity of motion and acceleration of the computer-controlled motion platform to the rate of flow of the dispenser, such that the linear velocity of flow of thixotropic suspension equals or closely approximates that of the motion platform in the direction of travel. In some embodiments, a plurality of motion platforms can be coordinated with one or more dispensers, each dispensing a separate thixotropic suspension to form a bead of controlled volume on the solid substrate. In this way, multiple suspensions with different APIs can be dispensed in parallel to create a combination therapy of multiple active ingredients.

In some embodiments, the disclosed system can employ an algorithm that translates a dosage formula for one or more active ingredients to a volume of thixotropic suspension based on the concentration of the suspension. The parameters can then drive the dispensed volume and flow rate from the dispenser during the motion path of the motion platform to dispense the command dose of the API ingredient onto the substrate. In some embodiments, an algorithm can be used for selecting the optimal concentration of the API ingredients and/or the exit diameter of the dispenser check valve in the motion platform to ensure that the dispensed line is constrained to the boundaries of the substrate plane and constraining preform features.

The disclosed system can include a computer-controlled actuated pump to withdraw the seals of the pump into an integrated cleaning chamber, where the seals and the body of the pumping actuator can be flooded with water or other cleaning fluids to ensure that the pump is cleaned in place without disassembly.

After suspensions 15 have been deposited onto a surface of substrate 10, one or more coatings 20 can be applied over each surface of the suspension and substrate. The coatings function as taste-masking agents to improve the flavor of assembly 5. In addition, the coatings function to protect substrate 10 and/or thixotropic suspensions 15 from oxidation, exposure, and contamination from the surrounding environment (e.g., temperature, humidity, moisture).

Suitable coatings can include any solid or semi-solid edible material, including (but not limited to) chocolate, caramel, honey, nougat, syrup, nut butter, agave, syrup, yogurt, pudding, butterscotch, fruit purees, molasses, frosting, flavored polysaccharide films, marshmallow cream, and the like. In some embodiments, the coatings can include particulates, such as bran pieces, nuts, chocolate chips, coconut, and the like. The coatings can also include flavorings, such as cinnamon, sugar, and other flavors. Thus, the substrate/suspension unit can be enrobed with one or more edible coverings that encase the dosed APIs and add taste masking and/or organoleptic properties. As a result, the disclosed assembly has a palatable flavor, thereby encouraging daily consumption.

Coatings 20 can be applied using any desired method. For example, the coatings can be applied by spray coating, dip coating, bottom enrobing, fully enrobing, or drizzling on top of the substrate. Such methods are well known in the art.

Accordingly, the disclosed system includes a customized API formulation from data specific to a particular subject that facilitates the single dose oral delivery of one or more APIs, combined in a highly palatable custom mixture with food substances, flavors, and/or textures desired by the subject. In some embodiments, the method includes an automated formulation algorithm that uses correlation and relevance scores to create a list of known and available components for inclusion and proportioned dose of each in the custom mixture, derived from data captured in an individual subject's profile. The taste preference information received can be combined with medical records, test results, and/or genetic tests to compile a composite individual subject profile and preferences score. In some embodiments, the profile can be directly determined by a questionnaire, by online responses to a computer interface, and/or indirectly by other previously captured data sources specific to the subject. The subject's profile can further include information such as the subject's physical attributes and history data including weight, height, sex, age, and health status (e.g., pregnant, active, immobile, and the like). In some embodiments, the algorithm can be based on simple heuristics or more involved statistical methods, such as regression or machine learning.

Thus, the disclosed system and method includes APIs variably dosed by additive on demand manufacture in accordance with personalized formulations to match an individual medical or general health needs as single ingredient or combination therapy of multiple APIs, delivered as palatable oral formulations in a solid form. Individualized selection of APIs and variable dosing and combinations of ingredients, enables personalized medicine and nutrition. The formulation for an individual can be determined in accordance with a medical practitioner's prescription, or as may be formulated with a multivariable algorithm in which pharmacogenomic, nutrigenomic, biomarker indications, blood assays, or responses to questions and answers obtained from the individual are the data inputs. In some embodiments, an edible solid bar or wafer is made on demand that is convenient to consume, as it will be shelf stable in ambient environment, as an alternative to taking one or more pills. Further, to encourage adherence to therapies for an extensive period, patient and consumer populations are offered an alternative to multiple pills with a solid form that is made for once or twice daily consumption.

It should be appreciated that all components of the disclosed edible assembly are constructed from GRAS (generally recognized as safe) materials recognized by the U.S. Food and Drug Administration. In some embodiments, the GRAS materials are made from a variety of digestible proteins, fats, plant fibers, polysaccharides, starches, hydrocolloid, edible waxes, or any of these materials that form a gel or SOL matrix, such that it returns to a semi-solid state at rest, and liquifies under pressure.

Thus, the disclosed system can achieve high throughput, which is a major advantage over current 3D methods that are viable for active ingredients. The disclosed system includes independently controlled actuators that know the characteristics of the ingredient they are dispensing and have the ability to dispense multiple ingredients in parallel. The issue that this solves is that with different carriers for the APIs, obtaining the same flow rate on all that are in parallel requires different pressure differentials, nozzle diameters, and possibly thermal profiles. Pressure as generated by acceleration and velocity of the actuator will generate a different extrusion flow rate depending on the rheology of the composition so different levels of API blended into the same carrier, as well as emergent chemical bonding/repulsion can be accommodated by an adaptable control system. Thus, the disclosed system allows multiple channels of different ingredients to be uniformly extruded in parallel onto a common substrate.

The final solid assembly 5 can be dimensioned to be a single serving size for a subject, such as about 40 grams. However, the disclosed assembly is not limited and can be scaled up or down to include any desired dimensions. Assembly 5 can be stored in a pouch or other container for weeks or months, without inducing active leakage or interaction with the substrate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Determination of Dispensing Lengths for 82 mg Aspirin 5 beads of 82 mg of aspirin was dispensed on a bar with length of about 4.5 inches. The aspirin was dispensed at bead diameters of 10 mm (0.079 vol/mm), 8 mm (0.050 vol/mm), 7 mm (0.038 vol/mm), 6 mm (0.028 vol/mm), and 4 mm (0.013 vol/mm) to determine the bead line and diameters for dispensing. The maximum bead line length was set at 100 mm to fit longitudinally the bar. As shown in Table 1 below, aspirin dosed at 82 mg fit in less than 100 mm in length at range of concentrations greater than 10 mg/ml and bead diameters of greater than 4 mm. Therefore, it was concluded that aspirin clearly can be dose on a bar of length 100 mm or more over a range of parameters. As shown in Table I below, green=fits on the bar, red=too long.

Figure 5:
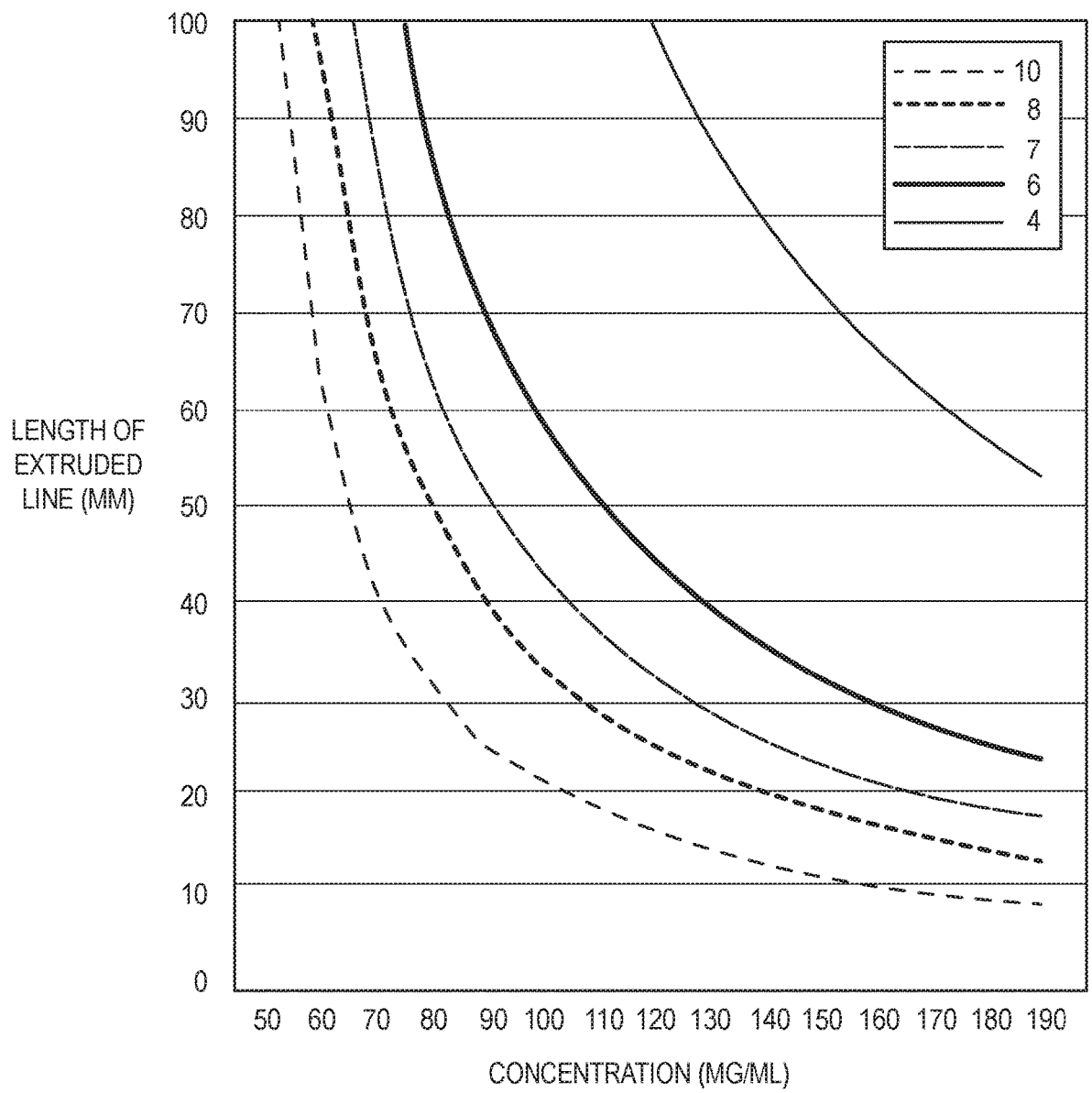
FIG. 5 is a line graph illustrating dispense length for 100 mg API per line at various densities and dispense bead diameters.

The data is illustrated graphically in FIG. 5. Particularly, the x-axis is concentration (mg/ml) and the y-axis corresponds to the length of extruded line to extrude a fixed dose of aspirin (50 mg total) at bead diameters of 4, 6, 7, 8, and 10 mm.

TABLE I

| 100 mg API Dispensing Length Studies | | | | | |
| --- | --- | --- | --- | --- | --- |
| vol/mm | 0.079 | 0.050 | 0.038 | 0.028 | 0.013 |
| Bead diam (mm) | | | | | 6 |
| Concentration (mg/ml) | | | | | |
| 10 | 104.41 | 163.13 | 213.07 | 290.02 | 652.54 |
| 20 | 52.20 | 81.57 | 106.54 | 145.01 | 326.27 |
| 30 | 34.80 | 54.38 | 71.02 | 96.67 | 217.51 |
| 40 | 26.10 | 40.78 | 53.27 | 72.50 | 163.13 |
| 50 | 20.88 | 32.63 | 42.61 | 58.00 | 130.51 |
| 60 | 17.40 | 27.19 | 35.51 | 48.34 | 108.76 |
| 70 | 14.92 | 23.30 | 30.44 | 41.43 | 93.22 |
| 80 | 13.05 | 20.39 | 26.63 | 36.25 | 81.57 |
| 90 | 11.60 | 18.13 | 23.67 | 32.22 | 72.50 |
| 100 | 10.44 | 16.31 | 21.31 | 29.00 | 65.25 |
| 110 | 9.49 | 14.83 | 19.37 | 26.37 | 59.32 |
| 120 | 8.70 | 13.59 | 17.76 | 24.17 | 54.38 |
| 130 | 8.03 | 12.55 | 16.39 | 22.31 | 50.20 |
| 140 | 7.46 | 11.65 | 15.22 | 20.72 | 46.61 |
| 150 | 6.96 | 10.88 | 14.20 | 19.33 | 43.50 |

Example 2

Determination of Dispensing Lengths for 250 mg API

The same method set forth above in Example 1 was repeated for a nutritional combination that required higher average doses of aspirin (250 mg per line) with a bead length of less than 100 mm. The raw data is illustrated below in TABLE II and is illustrated graphically in FIG. 6.

TABLE II

| 250 mg API Dispensing Length Studies | | | | | |
| --- | --- | --- | --- | --- | --- |
| vol/ml | 0.079 | 0.050 | 0.038 | 0.028 | 0.013 |
| Bead diameter (mm) | 10 | 8 | 7 | 6 | 4 |
| mg/ml | | | | | |
| 10 | 127.32 | 198.94 | 259.84 | 353.68 | 795.77 |
| 20 | 63.66 | 99.47 | 129.92 | 176.84 | 397.89 |
| 30 | 42.44 | 66.31 | 86.61 | 117.89 | 265.26 |
| 40 | 31.83 | 49.74 | 64.96 | 88.42 | 198.94 |
| 50 | 25.46 | 39.79 | 51.97 | 70.74 | 159.15 |
| 60 | 21.22 | 33.16 | 43.31 | 58.95 | 132.63 |
| 70 | 18.19 | 28.42 | 37.12 | 50.53 | 113.68 |
| 80 | 15.92 | 24.87 | 32.48 | 44.21 | 99.47 |
| 90 | 14.15 | 22.10 | 28.87 | 39.30 | 88.42 |
| 100 | 12.73 | 19.89 | 25.98 | 35.37 | 79.58 |
| 110 | 11.57 | 18.09 | 23.62 | 32.15 | 72.34 |
| 120 | 10.61 | 16.58 | 21.65 | 29.47 | 66.31 |
| 130 | 9.79 | 15.30 | 19.99 | 27.21 | 61.21 |
| 140 | 9.09 | 14.21 | 18.56 | 25.26 | 56.84 |
| 150 | 8.49 | 13.26 | 17.32 | 23.58 | 53.05 |
| 160 | 7.96 | 12.43 | 16.24 | 22.10 | 49.74 |
| 170 | 7.49 | 11.70 | 15.28 | 20.80 | 46.81 |
| 180 | 7.07 | 11.05 | 14.44 | 19.65 | 44.21 |
| 190 | 6.70 | 10.47 | 13.68 | 18.61 | 41.88 |
| 200 | 6.37 | 9.95 | 12.99 | 17.68 | 39.79 |
| 210 | 6.06 | 9.47 | 12.37 | 16.84 | 37.89 |
| 220 | 5.79 | 9.04 | 11.81 | 16.08 | 36.17 |
| 230 | 5.54 | 8.65 | 11.30 | 15.38 | 34.60 |
| 240 | 5.31 | 8.29 | 10.83 | 14.74 | 33.16 |
| 250 | 5.09 | 7.96 | 10.39 | 14.15 | 31.83 |
| 260 | 4.90 | 7.65 | 9.99 | 13.60 | 30.61 |
| 270 | 4.72 | 7.37 | 9.62 | 13.10 | 29.47 |
| 280 | 4.55 | 7.11 | 9.28 | 12.63 | 28.42 |
| 290 | 4.39 | 6.86 | 8.96 | 12.20 | 27.44 |
| 300 | 4.24 | 6.63 | 8.66 | 11.79 | 26.53 |
| 310 | 4.11 | 6.42 | 8.38 | 11.41 | 25.67 |
| 320 | 3.98 | 6.22 | 8.12 | 11.05 | 24.87 |
| 330 | 3.86 | 6.03 | 7.87 | 10.72 | 24.11 |
| 340 | 3.74 | 5.85 | 7.64 | 10.40 | 23.41 |
| 350 | 3.64 | 5.68 | 7.42 | 10.11 | 22.74 |

Figure 6:
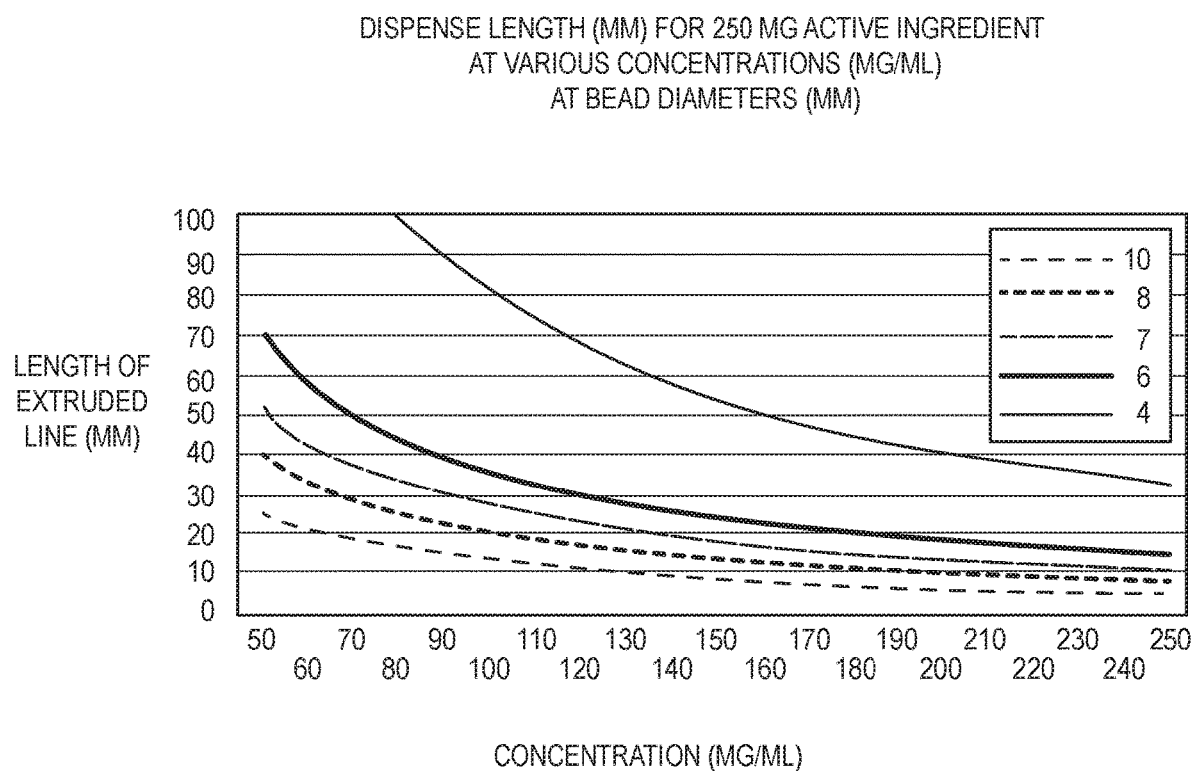
FIG. 6 is a line graph illustrating dispense length for 250 mg API per line at various densities and dispense bead diameters.

As shown in FIG. 6, most or all APIs would fit into some subset of the combination of concentration and bead diameter. The obvious potential is that a single substrate (API) can be stacked to achieve higher number of ingredients. For example, a 3 layer×5 line bar can have 15 ingredients, or a 6 line, 2 layer bar can have 12 ingredients. There are numerous tradeoffs and optimizations that can be calculated to achieve a total dose and number of APIs needed per bar.

What is claimed is:

1. A solid assembly for oral consumption, the assembly comprising:
   a substrate defining one or more depressions;
   two or more suspensions deposited within the depressions of the substrate, wherein each suspension comprises a homogenous dispersion of one or more active ingredients and a carrier,
   wherein the one or more active ingredients comprise at least one of an active pharmaceutical ingredient and a dietary supplement ingredient,
   wherein each suspension is viscous and/or thixotropic;
   one or more coatings applied over one or more surfaces of the substrate;
   wherein each active ingredient is dosed based on a formula that is determined for a specific subject consuming the solid assembly, wherein the formula is responsive to a preference or characteristic of an individual that will consume the solid assembly,
   wherein each of the two or more suspensions are configured as longitudinal beads,
   wherein a length of a first suspension of the two or more suspensions is different from a length of a second suspension of the two or more suspensions,
   wherein the first suspension comprises the at least one of an active pharmaceutical ingredient and a dietary supplement ingredient that is different than the second suspension.

2. The solid assembly of claim 1, wherein the substrate is comprised of protein fiber, carbohydrates, and lipid, and one or more of: fillers, pH adjusting agents, preservatives, anti-adhesives, plasticizers, opacifiers, coloring agents, pigments, surfactants, diluents, anti-foaming agents, lubricants, binders, granulating aids, taste modifying agents, and glidants.

3. The solid assembly of claim 1, wherein the depressions are configured as a plurality of longitudinal channels.

4. The solid assembly of claim 1, wherein the active ingredients are selected from one or more pharmaceuticals, vitamins, food supplements, or combinations thereof.

5. The solid assembly of claim 4, wherein the one or more pharmaceuticals are selected from compounds used for prevention, diagnosis, treatment, or cure of a chronic condition.

6. The solid assembly of claim 4, wherein the one or more vitamins are selected from thiamine, riboflavin, niacin, nicotinic acid, pantothenic acid, pyridoxine, biotin, folic acid, vitamin B6, vitamin B12, lipoic acid, vitamin C, vitamin A, vitamin D, vitamin E, vitamin K, and derivatives thereof.

7. The solid assembly of claim 4, wherein the one or more food supplements are selected from iron, calcium, selenium, iodine, magnesium, butylated hydroxytoleune (BHT), butylated hydroxyanisole (BHA), flavonoids, beta carotene, polyphenol, glutathione, *echinacea*, flaxseed, gingko, turmeric, L-arginine, L-glutathione, L-lysine, and combinations thereof.

8. The solid assembly of claim 1, wherein the one or more active ingredients are encapsulated into microspheres.

9. The solid assembly of claim 8, wherein the microspheres are selected from reservoir-type microspheres, matrix-type microspheres, or combinations of reservoir-type and matrix-type microspheres.

10. The solid assembly of claim 8, wherein the microspheres have a size of about 1200 µm or less.

11. The solid assembly of claim 1, wherein the carrier is selected from gelatin, polymeric glycosaminoglycan, agar, carrageenan, alginate, natural gum, carboxymethyl cellulose, xylitol, sorbitol, mannitol, glycerin, pectin, dextran, dextran derivative, pullulan, xanthan, xyloglucan, starch, hyaluronic acid, guar gum, locust bean gum, gellan, carboxy-methyl-cellulose, acacia gum, propylene glycol, polyethylene glycol, polypropylene glycol, poly(tetramethylene ether) glycol, or combinations thereof.

12. The solid assembly of claim 1, wherein the carrier is liquid or semi-solid.

13. The solid assembly of claim 1, wherein the carrier has a water activity (Aw) of about 0.95 or less.

14. The solid assembly of claim 1, wherein the carrier is aseptic.

15. The solid assembly of claim 1, wherein the one or more thixotropic suspensions have a shelf life of at least 14 days under refrigerated conditions of about 40° F.

16. The solid assembly of claim 1, wherein the one or more thixotropic suspensions have a shelf life of at least 300 days under refrigerated conditions of about 40° F.

17. The solid assembly of claim 1, wherein the one or more active ingredients are uniformly dispersed but undissolved within the carrier.

18. The solid assembly of claim 1, wherein the one or more coatings are solid or semi-solid.

19. A method of preparing a solid assembly for oral consumption, the method comprising:
depositing two or more thixotropic suspensions onto one or more depressions positioned on a surface of a solid substrate, wherein each thixotropic suspension comprises a homogenous dispersion of one or more active ingredients and a carrier,
wherein the one or more active ingredients comprise at least one of an active pharmaceutical ingredient and a dietary supplement ingredient; and
applying one or more coatings to one or more surfaces of the solid substrate,
wherein each active ingredient is dosed based on a formula that is determined for a specific subject consuming the solid assembly, wherein the formula is responsive to a preference or characteristic of an individual that will consume the solid assembly,
wherein each of the two or more suspensions are configured as longitudinal beads,
wherein a length of a first suspension of the two or more suspensions is different from a length of a second suspension of the two or more suspensions,
wherein the first suspension comprises the at least one of an active pharmaceutical ingredient and a dietary supplement ingredient that is different than the second suspension.

20. The solid assembly of claim 8, wherein the microspheres are homogeneously distributed within the thixotropic suspension.

21. The solid assembly of claim 3, wherein the thixotropic suspensions are stacked to achieve a higher total number of active ingredients, where stacking includes depositing a first layer of the one or more suspensions and depositing a second layer of the one or more suspensions on top of the first layer.

22. The method of claim 19, further comprising verifying the dose of each active ingredient in the solid assembly by a machine vision 3D volume scanner or structured light plane configured to ensure that the length and the volume of the suspension dispensed on the solid substrate satisfy the formula determined for the specific subject.

* * * * *